United States Patent
Yoo et al.

(10) Patent No.: US 7,169,434 B2
(45) Date of Patent: Jan. 30, 2007

(54) MOLECULAR PRESS DEHYDRATION METHOD FOR VEGETATIVE TISSUE USING THE SOLID PHASE OF WATER SOLUBLE POLYMER SUBSTANCES AS A DEHYDRATING AGENT

(76) Inventors: Myung-Shik Yoo, 1133-201, Jangmi Apartment, 1092, Sanbon-dong, Gunpo-city, 435-040 Kyunggi-do (KR); Hyun-Chang Seo, 2-502, Gwangiang Apartment, 38-1, Yoido-dong, Yeoungdeungpo-ku, 150-010 Seoul (KR)

(*) Notice: Subject to any disclaimer, the term of this patent is extended or adjusted under 35 U.S.C. 154(b) by 498 days.

(21) Appl. No.: 10/450,706

(22) PCT Filed: Sep. 2, 2002

(86) PCT No.: PCT/KR02/01651
§ 371 (c)(1), (2), (4) Date: Jun. 23, 2003

(87) PCT Pub. No.: WO03/039273
PCT Pub. Date: May 15, 2003

(65) Prior Publication Data
US 2004/0062843 A1  Apr. 1, 2004

(30) Foreign Application Priority Data
Nov. 9, 2001 (KR) .............................. 2001-69777

(51) Int. Cl.
*A23L 3/3463* (2006.01)
*A23L 3/42* (2006.01)

(52) U.S. Cl. ...................... 426/640; 426/573; 426/639; 426/656

(58) Field of Classification Search ................ 426/639, 426/573, 656, 640
See application file for complete search history.

(56) References Cited

U.S. PATENT DOCUMENTS 4,017,642 A * 4/1977 Orth et al. .................... 426/69
4,521,314 A    6/1985 Lundin et al.
6,268,012 B1   7/2001 Sikora et al.

FOREIGN PATENT DOCUMENTS

| JP | 53-81644  | * | 6/1978  |
| KR | 19882174  |   | 10/1988 |
| KR | 200113058 |   | 2/2001  |
| WO | 98/53711  |   | 12/1998 |

OTHER PUBLICATIONS

Choi Dong-Won et al., "A Study on Dehydration and Impregnation of Vegetables", The Korean Society of FoodScience and Technology, 1998, pp. 208-212.

* cited by examiner

*Primary Examiner*—Helen Pratt
(74) *Attorney, Agent, or Firm*—Greenblum & Bernstein, P.L.C.

(57) ABSTRACT

The present method is related to a molecular press dehydration method of vegetative tissues using water-soluble polymers in solid-phase as dehydrating agents. The molecular press dehydration method of the present invention is characterized by that dehydration is done by induction of cytorrhysis to vegetative tissues mixed with water-soluble polymers such as PEG, gum arabic, arabinogalactan, egg albumin, milk protein, soybean protein, etc. in its solid-phase. Compared to the conventional dehydration methods, the present method enables to obtain much greater dehydration effects in the amount and the rate, even though a very small amount of polymer substance is used; and the method enables to obtain excellent quality of dehydrated tissues as well as dehydrated exudates; and is environmentally friendly under favor of reduced energy consumption. The dehydrated vegetative tissues are excellent in their storage stability, and flavor and texture after rehydration, and dehydrated exudates are excellent in the concentrated useful components, flavor, and preservation quality. Therefore, the dehydrated vegetative tissues and exudates obtained by using the dehydration method of the present invention may be usefully applied to various fields such as foods and beverages, feeds, cosmetics, medicines, flavorings, agricultural chemicals, coloring agents, etc. according to the characteristics of plants.

12 Claims, 3 Drawing Sheets

| Cucumber | | | | | PEG | | |
|---|---|---|---|---|---|---|---|
| Sample | 100 | | | | Dehydrating agent | 100 | |
| Solids | 4.50 | | Dehydrated for 18 hours | | Solids | 99.97 | |
| Dehydrated tissue | 8.86 | | | | dehydrated exudates | | |
| | | | | | Filtration(glass filter) | | |
| Solids in dehydrated tissue | | | insolubles escaped from cucumber | | Solids of the exudate | | |
| 4.14 | | | 0.005 | | 100.33 | | |
| ↓ Rehydration | | | | | ↓ | | |
| Rehydrated tissue cucumber solids | | Rehydrated solution PEG penetration | | | Classified | | |
| | | | | | PEG in solution | soluble solids exuded from cucumber | |
| SI | | PI | | | PO | SO | |
| 1.69 | | 2.45 | | | 97.52 | 2.81 | |

Figure 1

| Cucumber | | | | | PEG | | |
|---|---|---|---|---|---|---|---|
| Sample | 100 | | | | Dehydrating agent | 100 | |
| Solids | 4.50 | | | | Solids | 99.97 | |
| | | | Dehydrated for 18 hours | | | | |
| Dehydrated tissue | 8.86 | | | | dehydrated exudates | | |
| | | | | | Filtration (glass filter) | | |
| Solids in dehydrated tissue | | | insolubles escaped from cucumber | | Solids of the exudate | | |
| 4.14 | | | 0.005 | | 100.33 | | |
| | Rehydration | | | | | | |
| Rehydrated tissue | | Rehydrated solution | | | Classified | | |
| cucumber solids | | PEG penetration | | | PEG in solution | soluble solids exuded from cucumber | |
| SI | | PI | | | PO | SO | |
| 1.69 | | 2.45 | | | 97.52 | 2.81 | |

Figure 2

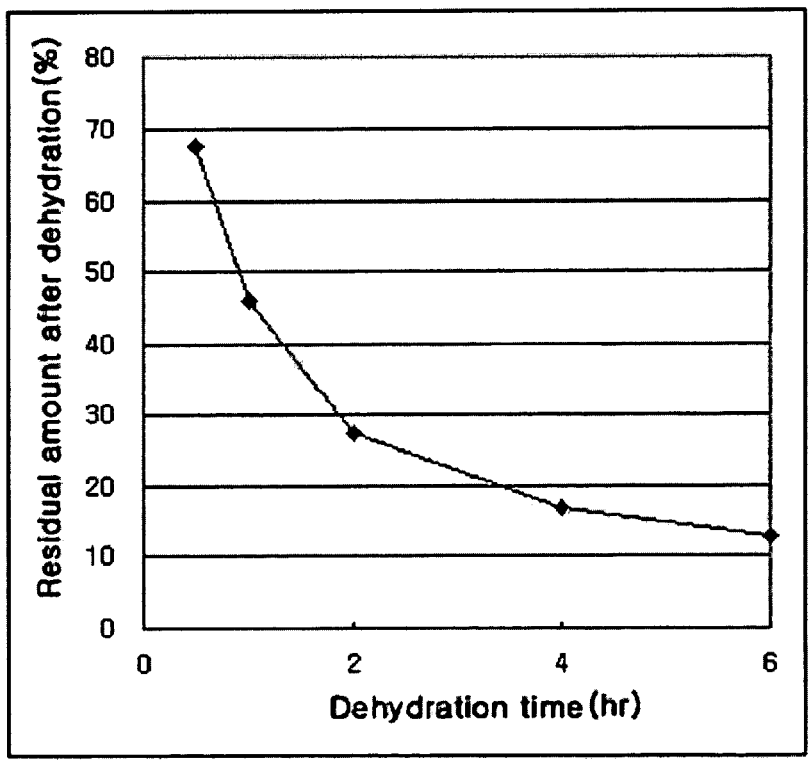

Before rehydration     After rehydration

Figure 5
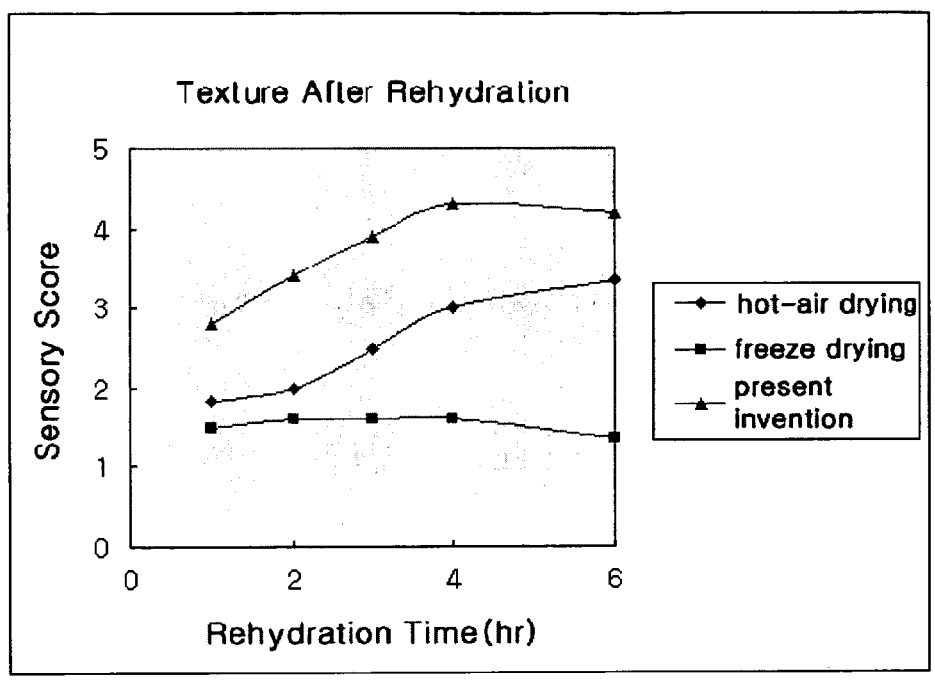
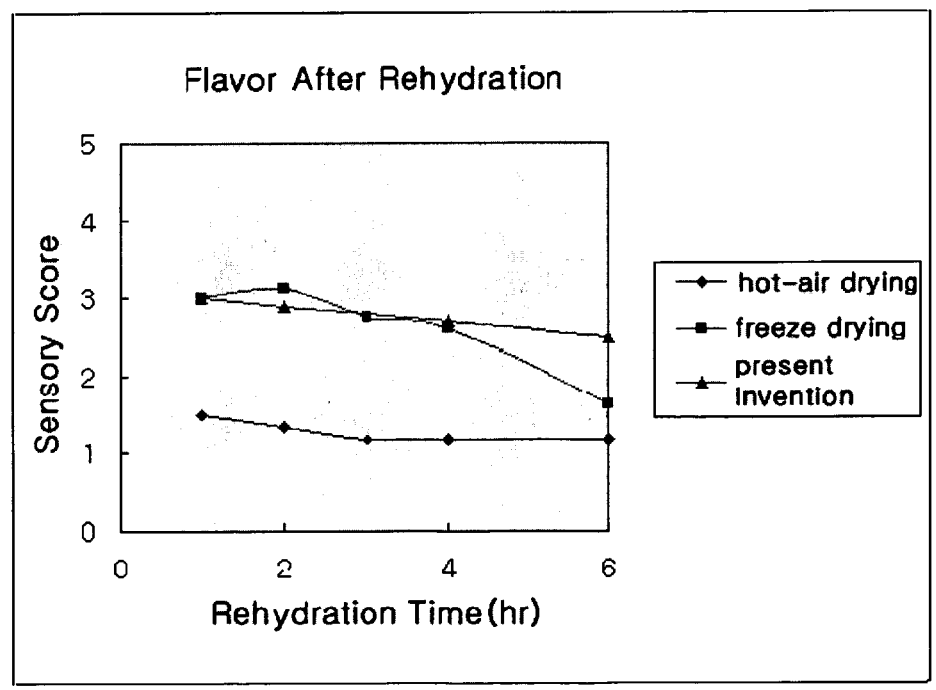

MOLECULAR PRESS DEHYDRATION METHOD FOR VEGETATIVE TISSUE USING THE SOLID PHASE OF WATER SOLUBLE POLYMER SUBSTANCES AS A DEHYDRATING AGENT

BACKGROUND OF THE INVENTION

1. Field of the Invention

The present invention is related to a molecular press dehydration method of vegetative tissues. Dehydration of vegetables is a very useful technology for the manufacture and development of foods and beverages, feeds, cosmetics, and pharmaceuticals.

2. Description of the Prior Art

Traditional dehydration and drying methods of vegetative tissues include osmotic dehydration, hot-air drying, freeze drying, etc. In osmotic dehydration, water of hypotonic solution in cytoplasms transfers to the hypertonic solution of a dehydrating agent through semipermeable cell membranes. In this method, immersion of vegetables into the concentrated dehydrating solution induces dehydration by the gradients of concentration between cell membranes. Included in this method are salting using salts such as the table salt, etc. and sugaring using sugars such as sucrose, etc. as dehydrating agents.

This method is advantageous in that the initial dehydration rate is high. However, it is disadvantageous in that the final amount of dehydration is small because most of transferred water remains in the cell wall by rapid shrinking and destruction of cell membranes, and dehydration is stopped immediately after the dehydrating agent is diffused into the cell wall and there is no difference in the concentrations of dehydrating agents in and out of the cells. Also, a large amount of the dehydrating agent penetrated into the cell wall reduces the rate of drying after dehydration due to a lowered water activity by the solute of the dehydrating agent, and it affects the taste of dehydrated tissues adversely, and lowers rehydration quality of tissues after drying as the dehydrating agent denatures cell wall components during dehydration. Further, the quality of tissues is lowered as useful components of dehydrated tissues are reduced since a large amount of cell fluid components flows out of the cells due to destruction of cell membranes during dehydration. Therefore, this method is used for the preservation of dehydrated tissues with a dehydrating agent as in salting or sugaring, reducing the dehydration time, and partially as the pre-step of drying for improving the quality of dried tissues.

Hot-air drying is a traditional dehydration method for vegetative tissues by heated dry air. This method is advantageous in view of the cost, but it is difficult to use it for processing high-grade food due to deterioration of the quality such as colors, flavors, and texture of dehydrated tissues.

Freeze drying is a method of freezing vegetative tissues rapidly followed by drying them by sublimation under a high vacuum. The quality of food is maintained excellently since food components are changed less compared to other methods. However, the texture of tissues is damaged greatly since cell tissues are destroyed by freezing and the processing cost is high. It is therefore used only for processing of some high-grade foods.

Accordingly, it is necessary to intent a dehydration method of vegetative tissues in which vegetative tissues may be dehydrated and dried at a low cost and a high yield, the original quality and value may be maintained when rehydrating the dehydrated tissues, and dehydrated tissues and extudates may be utilized more efficiently.

Another principle that can be applied to dehydration of vegetative tissues is a cytorrhysis phenomenon. Cytorrhysis is a biological phenomenon that is also called collapse of the cell wall. The cells could be dehydrated as they are contracted and distorted by the diffusion pressure of polymer molecules applied to the cell wall where the polymers are unable to be penetrated into the cell wall if their sizes are greater than those of the pores of the cell wall when vegetative tissues are in the concentrated solution of water-soluble polymers.

Dehydration by cytorrhysis is similar to the conventional osmotic dehydration in that dehydration is done by using the solutes outside of the cells, but is different from that in that the polymers used for cytorrhysis remain outside of the cell as they are greater than the pores of the cell wall while the solutes may be transferred through the pores of the cell wall in osmotic dehydration. Therefore, a large amount of moisture is dehydrated in dehydration using cytorrhysis compared to osmotic dehydration since the gradients in concentration in and out of the cells are maintained continuously, while dehydration is stopped in osmotic dehydration when there is no difference in concentration in and out of the cells as the solutes are transferred into the cells.

As a dehydration method by cytorrhysis, it has been reported that the polyethylene glycol (hereinafter referred to as PEG) solution having various molecular weights has been used for dehydration of potato tissues (Dong-Won Choi, A study on dewatering and impregnation soaking process of potato, 1998). The results of the above study suggest that the cytorrhysis phenomenon is more useful for dehydration compared to the conventionally used principle of osmotic pressure since dehydration by cytorrhysis begins in the PEG solution having a molecular weight of 600 or greater and the typical cytorrhysis phenomenon is shown in the PEG 4000 solution and the amount of dehydration is greater than that with salt.

The above study on the material balance is conducted on the assumption that vegetable solids do not flow out to the outside during dehydration. Actually, it is shown that a considerable amount of vegetable solids flows out to the dehydrating solution during dehydration by cytorrhysis. Therefore, the cytorrhysis phenomenon and the amount of dehydration measured from the material balance suggested in the above study may not be accurate, and what is known is that the greater the molecular weight of PEG is, the more evident the cytorrhysis phenomenon is, and the higher the PEG concentration of the aqueous solution is, the greater the amount of dehydration is.

It is difficult to manufacture a concentrated water-soluble polymer solution as the greater the molecular weight is, the lower the solubility is, and it is difficult to expect an effective dehydration unless a large amount of polymers to the degree of 5–10 times of fresh vegetables is used since the dehydrating solution is diluted by water coming out of tissues during dehydration. In the above study, only the concentration of the PEG solution used actually for the experiment is suggested, but other matters such as the ratio of PEG to vegetables used, etc. are not published.

Further, it is no less important to increase the preservation quality and utilization of dehydrated exudates than to preserve and utilize dehydrated tissues since a large amount of water-soluble components flows out during dehydration. However, in the method used in the above study, it is easy for the exudates to be spoiled by microorganisms since the concentration of useful components exuded is very low and the water activity is increased during dehydration as the dehydrating solution is diluted gradually. Therefore, there is a problem of not being able to utilize the exudates effectively since the exudates are spoiled and the quality of dehydrated exudates is lowered.

Accordingly, there remain many subjects to study until the cytorrhysis phenomenon is applied to and practiced for the dehydration of vegetative tissues. Proposed in the present invention is an effective method of dehydration of vegetative tissues according to the principle of cytorrhysis.

SUMMARY OF THE INVENTION

The present invention is related to a method of molecular press dehydration of vegetative tissues using solid-phase water-soluble polymers as dehydrating agents.

The solid phase in the molecular press dehydration method in the present invention refers to the state of crystals or powder. And, it refers to a dispersion in which a part of polymers is dispersed in the solid state such as crystals or powder where more polymers than necessary to be a saturated solution are mixed with water.

The molecular press dehydration method of the present invention has a much superior dehydration effect by using solid-phase dehydrating agents only with about ⅕ to 1/10 of polymers compared to the conventionally used aqueous solution. Although crystals or powder generally show a higher dehydration efficiency compared to that of a dispersion, a dispersion is more effective than crystals or powder for the initial dehydration and the tissues with a large surface area. The surface of tissues may be covered evenly with a dispersion. Particularly, the dehydration effect may be promoted by adjusting the concentration of the dispersion for the tissues such as leaves, etc.

If solid-phase polymers are used, at the beginning, they are dissolved by moisture on the surface of vegetative tissues and dehydration occurs. Since the polymers are dissolved continuously by water coming out of the tissues as dehydration is progressed, vegetative tissues are in the saturated solution throughout the process of dehydration, and it is possible to sustain dehydration effectively and to prevent change in the quality.

Since dehydration may be done without damaging cellular tissues by using solid-phase polymers, it is possible to avoid enzymatic browning since polymer components such as enzymes in the cells do not flow out of the tissues to be dehydrated. Also, it is possible to reduce oxidative browning since direct exposure of vegetable components to the air is prevented as the surface of tissues is covered with high-molecular-weight dehydrating agents through dehydration and drying periods.

If solid-phase polymers are used, exuded vegetable components are not diluted in dehydrated exudates maintaining the concentration in the original plant tissues almost as is, and the exudates are extracted with the flavor of fresh tissues kept as is and without being changed by enzymes or oxidation. Also, it is possible to preserve non-spoiling dehydrated exudates in a fresh state without addition of a preservative, pasteurization processing, etc. as putrefaction of dehydrated exudates due to the microbial growth is prevented since the water activity is lowered by maintaining the concentration of high-molecular-weight dehydrating agents in the almost saturated state.

It is preferable that water-soluble polymers used for the molecular press dehydration method of the present invention to have a molecular size which is greater than the pore size of the cell wall of plant cells, to have a large solubility in water so that a concentrated solution can be made, and to have a low viscosity when they are dissolved in water so that diffusion of molecules is facilitated.

Water-soluble polymers that can be used for molecular press dehydration of the present invention include PEG, gum arabic, arabinogalactan, egg albumin, milk protein, soybean protein, etc.

PEG, which is a synthetic polymer, is a proper material for cytorrhysis since it has a large solubility in water and its aqueous solution has a low viscosity. Preferably, PEG having the molecular weight of 3,400 or greater is used. In using the PEG solution, the cytorrhysis phenomenon begins to occur when the PEG solution having a molecular weight of 1,500 or greater is used. Only the partial contraction of cells occurs when PEG having a molecular weight of up to 2,000 is used, and the dehydration phenomenon occurs as the cells are contracted significantly when the PEG solution having a molecular weight of 3,400 or greater is used.

Gum arabic, arabinogalactan, and egg albumin are dissolved readily in water and have a low viscosity, and therefore, induce the dehydration phenomenon by cytorrhysis easily. Although milk protein and soybean protein have a low solubility in water and their solutions have a rather high viscosity, they can induce dehydration by cytorrhysis and show a greater dehydration effect than in osmotic dehydration.

The amount of a polymer which is necessary for the molecular press dehydration method of the present invention is ⅕ to 1/10 times of the amount which is necessary for using it in the aqueous solution, i.e., only about the same amount as that of a plant material or less, and this amount may be adjusted within the above range according to the moisture content contained in individual plant tissue inherently.

The molecular press dehydration method of the present invention is characterized by obtaining dehydrated tissues and exudates through filtration or centrifugation after dehydration of vegetative tissue mixed with water-soluble polymers that can induce cytorrhysis in the solid-state.

In the present method, it is possible to increase the efficiency for dehydration by adding a dehydration aid or a pH modifier, differing the method of cutting the plant material, controlling the dehydration temperature, or washing the dehydrated tissues.

It is possible to increase the initial dehydration speed by mixing a low-molecular-weight dehydration aid to the polymer to eliminate the turgor pressure of vegetative tissues and accelerate exudation of moisture at the beginning of dehydration. Salts, sugars, or sugar alcohols that have been used for the conventional osmotic dehydration method may be used for low-molecular-weight dehydration aids.

Mixing a pH modifier to the polymer minimizes change in the quality such as discoloration, etc. that may occur due to the change in pH by exuded components during dehydration or by the addition of a dehydrating agent. For a pH modifier, an inorganic acid and alkali such as hydrochloric acid, sulfuric acid, sodium hydroxide, etc., or an organic acid such as acetic acid, citric acid, malic acid, tartaric acid, etc. or any of their salts may be used.

In the present method, it is possible to increase the speed and amount of dehydration by adjusting the temperature of dehydration to 45–65° C.

It is also possible to increase the speed and amount of dehydration and the speed of rehydration by maximizing the surface area that can come in contact with the polymer by cutting the plant material to be dehydrated thinly or cutting it in a direction facilitating diffusion of the polymer.

In the present method, dehydrated tissues and exudates are separated from each other by filtering or centrifugation of the dehydrated tissues. The dehydrated tissues may be used as they are or ground to be a paste.

Further, a considerable amount of the dehydrating agent remaining on the surface of dehydrated tissues may be removed by washing the dehydrated tissues promptly with water, concentrated dehydrating solution with a lowered viscosity, concentrated sugar with a low viscosity or salt solution after the dehydrated tissues are filtered or separated with a centrifuge. Although washing the dehydrated tissues again with water, etc. may seem to be contradictory to its original purpose, the moisture penetrated into the tissues can be dried easily as the penetration speed of moisture into the tissues during washing is slow and a part of moisture penetrated into the tissues remains only on the surface of the tissues.

Therefore, in the present method, the washing process prevents adhering of tissues during drying by removing a considerable amount of the dehydrating agent remaining on the surface of tissues without greatly affecting drying of tissues, and rather facilitates drying in some cases by preventing formation of the films of the dehydrating agent on the surface of tissues during drying. Also, it is possible to improve the appearance and quality of dried tissues by preventing the crystal formation of the dehydrating agent on the surface of dried tissues and by reducing the amount of the dehydrating agent remained in dried tissues through the washing process.

The tissues obtained by the dehydration method of the present invention are dried readily simply by being exposed to warm air or hot air or left in ambient air at a room temperature without using the conventional drier that has been used for drying of vegetative tissues. In a large-scale process, the rate of drying may be increased by using a machine that can perform centrifugation, washing, dehydration, and drying continuously. But the tissues may be dried easily even when they are left at a room temperature without a separate process although the drying speed is low compared to that in the above. The remaining moisture is evaporated easily since only a small amount of moisture remains in the tissues as most of moisture is dehydrated out of the cells without damaging cellular tissues and the resistance to the transfer of moisture in tissues, not in cells, is negligible. Also, the polymers remaining in the tissues may prevent browning since they protect the tissues from being exposed directly to the air, and they prevent spoilage by microorganisms.

Accordingly, the molecular press dehydration method of the present invention may have the maximum dehydration effect while using the minimum amount of polymers, and increase the quality and preservation ability of not only dehydrated tissues but also dehydrated exudates.

The movement of solids in vegetative tissues when the molecular press dehydration method of the present invention is used, i.e., the material balance during dehydration by the cytorrhysis, is shown in FIG. 1, where the method of measurement of the material balance is as follows:

Cucumbers, of which solids are measured, are mixed with the PEG 4000 powder at a ratio of 1:1, dehydrated for 18 hours, and separated into dehydrated tissues and dehydrated exudates with a centrifuge. The movement of solids is measured by separating the penetrated PEG in tissues from pure cucumber tissues by rehydrating the dehydrated tissues and eluting PEG completely in water. For the dehydrated exudates, the movement of each solid content is calculated by measuring the amount of minute insolubles obtained by filtration of the dehydrated exudates.

In FIG. 1, if it is assumed that the water-soluble solids of cucumbers are exuded sufficiently only in the dehydration procedure but are not exuded further in the rehydration procedure of dehydrated tissues, the difference between the amount of the total solids in the original tissues (ST) and of the solids in the tissues after rehydration (SI) is the solids exuded during dehydration (SO), and the solids eluted during rehydration are PEG solids penetrated into the tissues (PI). Therefore, the amount of solids in the dehydrated exudates is the sum of the residual PEG solids (PO), i.e., the original total PEG solids (PT) minus the penetrated PEG solids (PI), and eluted solids of cucumbers (SO).

Total solids of cucumbers $(ST)=SI+SO$

Total solids of $PEG(PT)=PI+PO(PO=PT-PI)$

Solids in dehydrated tissues$=SI+PI$

Solids in the dehydrated exudates$= PO+SO(=PT-PI+SO)$

The amount of escaped insoluble cucumbers in the dehydrated solution is an insignificant amount of 0.01% or less. And the amount of solids of cucumbers eluted during rehydration is excluded from calculation since it is considered to be a negligible amount compared to the total amount of solids in view of the color and smell of eluted solution.

As shown in FIG. 1, the results of calculation by the above method show that, among the 4.5 parts of the total solids of 100 parts of cucumbers, 2.81 parts (62.4%) are exuded to the dehydrated exudates and only 1.69 parts (37.6%) remain in the tissues, and 2.45 parts (59.2%) among 4.14 parts of solids of dehydrated tissues are PEG solids penetrated. That is, during dehydration by cytorrhysis, a large amount of PEG is penetrated into the space of tissues around the cells although it does not penetrate into the cells. And a large amount of water-soluble solids in the cells is exuded to the dehydrated exudates.

Therefore, during dehydration of vegetative tissues, useful components of vegetative tissues may be utilized to the maximum without loss only by increasing the preservation quality and applicability of not only dehydrated tissues but also dehydrated extracts such as the dehydrated exudates, etc. In view of this, the molecular press dehydration method of the present invention is very effective in that the preservation ability and storage stability of both of dehydrated tissues and dehydrated extracts may be reinforced by using a solid-phase dehydrating agent.

In the molecular press dehydration method of the present invention, the dehydrated tissues are revived in a state which is near to fresh tissues when they are rehydrated in water since dehydration is done without damaging cellular tissues so as not to denature cell wall components. The rehydration quality of dehydrated food is increased as the dehydrating agent remained in the tissues is removed almost during rehydration since the dehydrating agent of polymers penetrated into the intercellular space of tissues is eluted out of the tissues again.

Also, the dehydrated tissues and dehydrated exudates obtained by the molecular press dehydration method of the present method have much more superior quality in color, flavor, texture, etc. and diverse application areas than those obtained in the conventional method. The dehydrated tissues and exudate obtained by the molecular press dehydration method of the present invention may be utilized as follows, where the examples of utilization listed below are for the illustration of utilization only, and are not limited to those listed below:

Dehydrated tissues obtained by the molecular press dehydration method of the present invention may be used as follows:

Firstly, they may be used for the manufacture of beauty packs using aloe, cucumbers, potatoes, etc. by using useful components eluted from the tissues after rehydration since solids of the vegetables are kept well in the tissues. They may be also used for the manufacture of powdered teas of ginseng, ginger, *Codonopsis lanceolata*, etc. where the vegetable components are infused by rehydration, and of the sugared food and fruits by penetrating necessary components into dehydrated tissues when the tissues are rehydrated in the concentrated solution such as sugar, etc.

They may be further used for the manufacture of less irritative tobaccos, less sour tangerines, diet foods reduced in sugar and substituted with sugar alcohols, etc. by means of the fact that a specific component is exuded out of the tissues and reduced in the tissues during dehydration.

They may be further used for the manufacture of vegetables for soups, powdered soups, instant spices for rehydration, etc. that are used for instant foods, since they can be rehydrated to be tasted in the fresh texture as is, and of instant rice, instant porridge, etc. as it is possible even for the processed and cooked food tissues to be rehydrated after they are dehydrated as well.

In the meantime, dehydrated exudates obtained by the molecular press dehydration method of the present invention may be used as follows:

Firstly, dehydrated exudates with the natural flavor kept as is may be used for the manufacture of teas using fresh ginseng, seasonings using herbs or vegetables, flavorings using fruits, etc.

Secondly, the dehydrated exudates of aloe, cucumbers, and potatoes effective for beauty may be used for the raw material of skin beauty and pharmaceuticals. And also, the dehydrated exudates of red peppers may be used for the effective ingredient of ointments for the treatment of arthritis.

In case of various medicinal herbs, it is possible to search for the components having new effects and efficacy by dehydrating and extracting fresh tissues without changing their components contrary to the conventional method of extraction.

In case of the plants having the antimicrobial or insecticidal effects, the dehydrated exudates of garlic may be used for antimicrobial agents and insect repellants, while those of tobacco leaves and chrysanthemum may be used for the natural agricultural chemicals since they may be used for pesticides.

In case of plants that are used for the extraction of natural pigments, it is possible to extract pigments having a superior preservation quality economically in a simpler method than the conventional of solvent extraction method.

BRIEF DESCRIPTION OF THE DRAWINGS

The foregoing and other objects, aspects, and advantages will be better understood from the following detailed description of a preferred embodiment of the invention with reference to the drawings, in which:

FIG. 1 is a diagram showing the material balance when cucumber tissues are dehydrated with PEG 4000;

FIG. 2 is a graph showing the yield of dehydration according to the time when cucumber tissues are dehydrated by using gum arabic for a dehydrating agent;

FIGS. 5a and 5b are the graphs showing the results in average of sensory evaluation of the texture and flavor after rehydration of dehydrated tissues by using the molecular press dehydration method of the present invention, hot-air drying method, and freeze drying method.

DETAILED DESCRIPTION OF A PREFERRED EMBODIMENT OF THE INVENTION

The molecular press dehydration method of the present invention using gum arabic is illustrated in a preferred embodiment as follows:

Cucumber tissues are dehydrated and the efficiency of dehydration is measured by using gum arabic in order to confirm if it is possible to dehydrate vegetative tissues by the molecular press dehydration method of the present invention using gum arabic.

Gum arabic in the amount of 75% of that of cucumber tissues is mixed with cucumber tissues that are sliced to have a thickness of 1.5 mm, and the mixture is dehydrated while it is left alone for 30 minutes, 1 hour, 2 hours, 4 hours, and 6 hours, respectively. After it is dehydrated, it is washed with water twice promptly, and separated with a centrifuge for 5 minutes. The remaining amount of dehydration is measured, and the result is shown in FIG. 2.

As shown in FIG. 2, dehydration is progressed rapidly for up to 2 hours from 30 minutes after gum arabic and cucumber tissues are mixed, and the dehydration phenomenon is maintained continuously for up to 6 hours. Accordingly, it is seen that dehydration may occur efficiently by the molecular press dehydration method of the present invention, where gum arabic may be used for a excellent molecular press dehydrating agent.

Next, the effects of the molecular press dehydration method of the present invention using a solid-phase polymer and of the dehydration method using its aqueous solution are compared with each other. In order to confirm the effect of the molecular press dehydration method of the present invention using a solid-phase polymer, the amount of dehydration by this method is compared with that of the conventional method of dehydration using its aqueous solution.

PEG 4000 is selected for a dehydrating agent, and each type of crystals, powder, suspension, and saturated aqueous solution is prepared for. PEG 4000 crystals on the market are selected, and the amount of one time of the amount of cucumbers is used. For the PEG powder, PEG 4000 crystals are ground with a pulverizer, and the same amount is used. For the PEG 4000 suspension, to the saturated solution in which the PEG in the amount of the same amount of cucumbers is dissolved, the same amount of the PEG crystals is added. For the saturated PEG 4000 aqueous solutions (55 weight %), the saturated aqueous solution in which the PEG in the amount of the same and 5 times of the amount of cucumbers is dissolved are used.

The residual amount of dehydration is measured at regular intervals for 8 hours after cucumbers are immersed in or mixed with each type of PEG. The residual amount is measured without washing with water but after centrifugal separation for 5 minutes, of which results are shown in FIG. 3.

Figure 3:
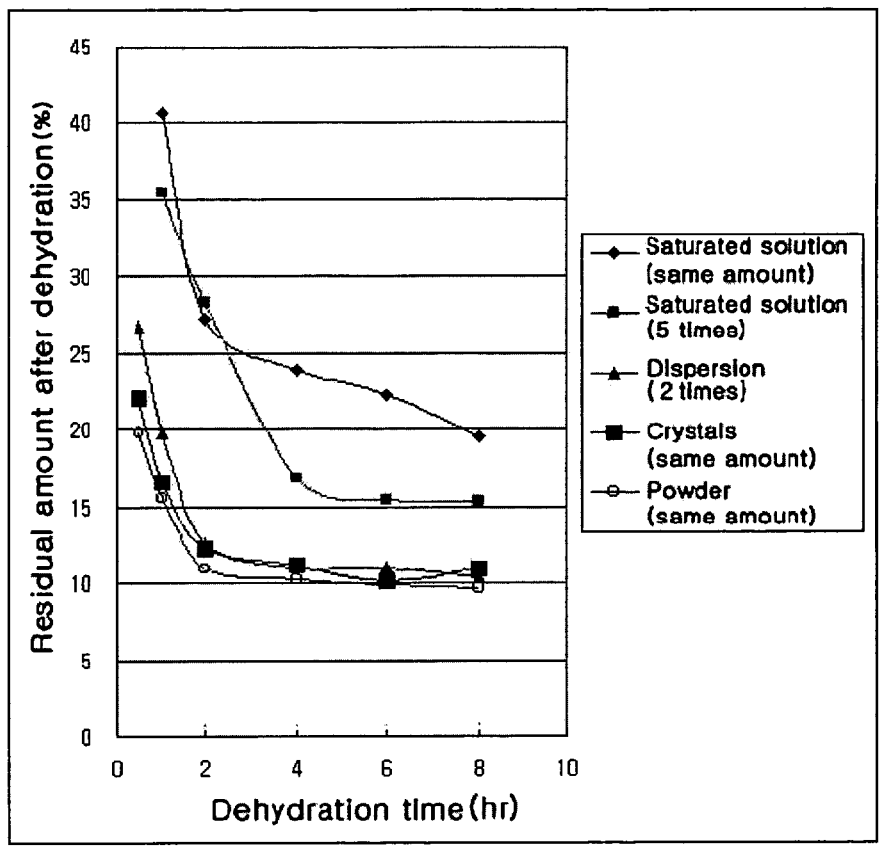
FIG. 3 is a graph in which the effects of dehydration when cucumber tissues are dehydrated by the molecular press dehydration method of the present invention and by the dehydration method using the aqueous solution with PEG 4000 are compared.

As shown in FIG. 3, the remaining amount of dehydration, i.e., the weight of tissues remained after dehydration and centrifugal separation, is reduced greatly when the suspension and solid-state crystals and powder are used compared to the case that saturated aqueous solutions are used.

As to the amount of PEG used, using the suspension and solid-state crystals and powder is very efficient economically since it is necessary to use only about ⅕ of PEG compared to the case of using saturated solutions. And this method takes a shorter drying time after dehydration and has a excellent rehydration quality.

Accordingly, compared to the method of dehydration using an aqueous solution, the molecular press dehydration method of the present invention using a suspension or a solid-phase polymer has a much more superior dehydration effect even when a very small amount of a dehydrating agent is used.

Then, the rehydration quality of the tissues obtained according to the molecular press dehydration method of the present invention is measured. The tissues used include those of radishes, carrots, potatoes, garlic, green onions, cucumbers, pimentos, apples, and aloe. After they are dehydrated by using the molecular press dehydration method of the present invention, they are rehydrated in water at a room temperature. The appereances of pimiento tissues, among them, prior to and after rehydration are shown in FIG. 4.

Figure 4:
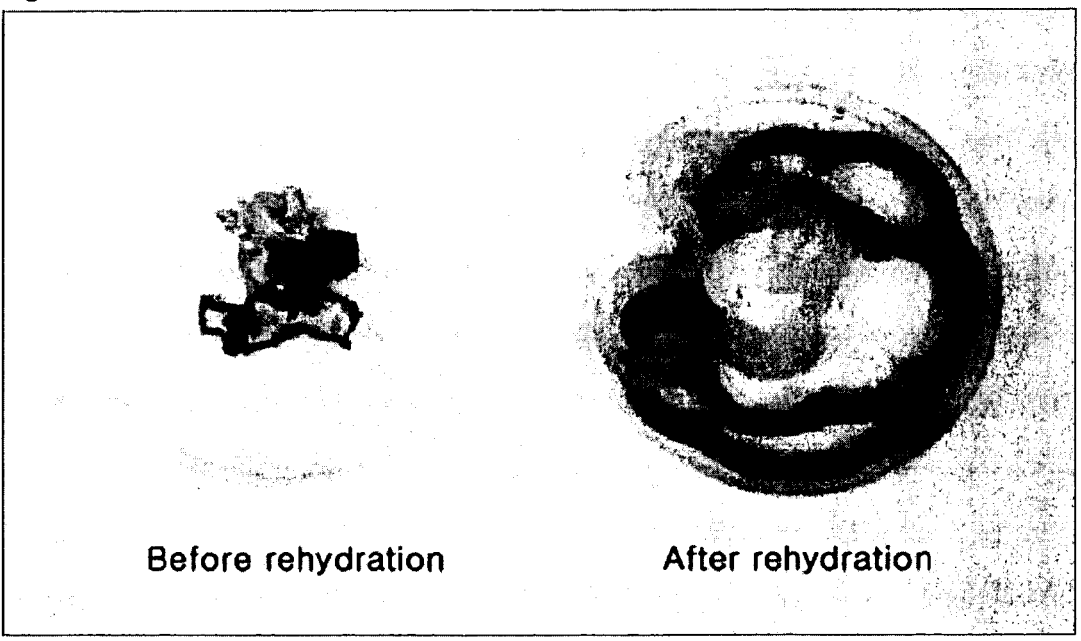
FIG. 4 is an illustration in which the appearance of tissues prior to and after rehydration of dehydrated pimento tissues by using the molecular press dehydration method of the present invention are compared.

As shown in FIG. 4, it is confirmed that pimiento tissues obtained according to the molecular press dehydration method of the present invention show a excellent rehydration quality when they are rehydrated in water.

In order to compare the rehydration quality of the molecular press dehydration method of the present invention with those of other methods of dehydration, vegetative tissues of the kinds used in the above are dehydrated according to each of the dehydration method of the present invention, hot-air drying method, and freeze drying method. The weight of rehydrated tissues separated through a centrifugal separator for 5 minutes after rehydration of each time is divided by the dried solids of each dehydrated tissue, and this value is referred to as the multiple of rehydration. The results are shown in Table 1. For the original tissues, it is a greater multiple of rehydration than that shown in Table 1 since the multiple of rehydration of dehydrated tissues using the molecular press dehydration method of the present invention is the comparison of the weight of the rehydrated tisuues not to the dried weight of original tissues but to the dried weight of dehydrated tissues, i.e., the sum of the PEG solids penetrated into the tissues and vegetable solids in dehydrated tissues.

TABLE 1

| Vegetalbe | Dehydration method | 1-hour rehydration | 2-hour rehydration | 3-hour rehydration | 4-hour rehydration. | 6-hour rehydration |
|---|---|---|---|---|---|---|
| Radishes | Present invention | 19.9 | 20.0 | 19.8 | 19.4 | 19.4 |
|  | Hot-air drying | 10.8 | 12.8 | 14.5 | 16.1 | 16.1 |
|  | Freeze drying | 18.5 | 18.4 | 19.5 | 18.0 | 18.1 |
| Carrots | Present invention | 9.3 | 10.1 | 11.3 | 10.5 | 9.6 |
|  | Freeze drying | 5.4 | 6.3 | 6.1 | 6.5 | 5.9 |
| Potatoes | Present invention | 4.3 | 4.3 | 4.3 | 4.2 | 4.1 |
|  | Hot-air drying | 3.6 | 3.6 | 3.7 | 3.6 | 3.7 |
|  | Freeze drying | 2.9 | 3.1 | 2.6 | 3.0 | 3.2 |
| Garlic | Present invention | 2.5 | 2.5 | 2.6 | 2.5 | 2.4 |
|  | Hot-air drying | 2.6 | 2.7 | 2.6 | 2.6 | 2.6 |
| Green onions | Present invention | 8.9 | 9.3 | 8.7 | 8.0 | 9.3 |
|  | Freeze drying | 7.3 | 6.0 | 8.0 | 7.5 | 8.4 |
| Cucumbers | Present invention | 17.6 | 19.1 | 19.1 | 19.5 | 17.1 |
|  | Hot-air drying | 5.4 | 7.3 | 9.3 | 11.4 | 14.6 |
| Pimentos | Present invention | 6.9 | 9.7 | 9.4 | 12.7 | 13.4 |
|  | Freeze drying | 5.6 | 5.4 | 6.9 | 5.5 | 5.6 |
| Apples | Present invention | 12.1 | 12.3 | 10.2 | 10.9 | 12.4 |
|  | Hot-air drying | 4.5 | 4.2 | 4.4 | 5.0 | 4.6 |
|  | Freeze drying | 2.6 | 2.6 | 2.3 | 2.4 | 2.3 |
| Aloe | Present invention | 12.8 | 15.8 | 16.9 | 17.6 | 19.1 |
|  | Hot-air drying | 7.5 | 8.6 | 8.3 | 9.2 | 9.0 |
|  | Freeze drying | 6.1 | 5.7 | 5.7 | 6.5 | 5.3 |

As shown in Table 1, it is seen that, in all vegetative tissues, the multiple of rehydration is greater when employing the molecular press dehydration method of the present invention than when employing the hot-air drying or freeze drying method. It is also seen that the rehydration is much faster when using the molecular press dehydration method of the present invention than when using the hot-air drying method although it is not faster than that of the freeze drying method.

Accordingly, it is seen that dehydrated tissues may be rehydrated efficiently in the molecular press dehydration method of the present invention compared to the conventional methods of dehydration.

In order to confirm the quality of tissues obtained by the molecular press dehydration method of the present invention, the texture and flavor of the rehydrated tissues in the above are evaluated.

The texture of each rehydrated tissue is measured by sensory evaluation, and the score of each tissue is determined according to the following scale of texture: (The texture is almost the same as that of fresh tissues: 5 points, considerably crispy: 4 points, crispy: 3 points, not particularly crispy: 2 points, and almost not crispy: 1 point.)

Also, the flavor of each rehydrated tissue is evaluated by sensory evaluation, and the score of each tissue is determined according to the following scale of flavor: (The flavor is very good: 5 points, good: 4 points, average: 3 points, weak: 2 points, and almost none: 1 point.)

The average values of the texture and flavor of tissues according to each dehydration method are computed and shown in FIG. 5.

In case of the texture, as shown in FIG. 5a, the texture after rehydration by the molecular press dehydration method of the present invention is shown to be more superior to those of the hot-air drying method or freeze drying method in all tissues in the above.

In case of the flavor, as shown in FIG. 5b, the flavor of tissues after rehydration by the molecular press dehydration method of the present invention is shown to be kept at a similar level to that of the freeze drying method which is known to keep the flavor of rehydrated tissues excellently and much more excellently than that of the hot-air drying method. Particularly, it is observed that the flavor is maintained continuously up to 6 hours during rehydration when the molecular press dehydration method of the present invention is used, while the keeping ability of the flavor is lowered after 4 hours in the freeze drying method.

Accordingly, it is seen that the texture of rehydrated tissues after dehydration by using the molecular press dehydration method of the present invention is much more superior to that of the tissues dried by the conventional methods, and dehydrated tissues of superior quality are obtained in that the flavor of tissues is kept at a high level to a degree similar to that of the freeze drying method even though a large amount of low-molecular-weight water-soluble materials are exuded during the dehydration process.

If vegetative tissues are dehydrated by using the molecular press dehydration method of the present invention, it is possible to obtain excellent results in all aspects of the final amount of dehydration, speed of dehydration, and the quality and preservation of dehydrated tissues and dehydrated exudates.

The molecular press dehydration method of the present invention enables to obtain dehydrated tissues of a much more superior quality at a high efficiency than that of the conventional dehydration method, and even dehydrated exudates that have been at a very inferior level in view of the quality and applicability in the conventional dehydration methods may be obtained to have a superior quality and a high preservation quality.

Compared to the conventional dehydration method using the aqueous solution, the molecular press dehydration method of the present invention is efficient economically since the amount of the polymer needed for dehydration is very small, and is environmentally friendly since the amount of energy to be consumed is reduced greatly as it is not necessary to have an additional heating or freezing process. Accordingly, dehydrated tissues and dehydrated exudates obtained by the molecular press dehydration method of the present invention may be usefully applied to various fields such as foods and beverages, feeds, beauty materials, medicine, flavorings, agricultural chemicals, coloring agents, etc. according to the characteristics of plants.

While the invention has been described in terms of a single preferred embodiment, those skilled in the art will recognize that the invention can be practiced with modification within the spirit and scope of the appended claims.

What is claimed is:

1. A method for dehydration of vegetative tissues, comprising mixing a solid-state water-soluble polymer with the vegetable tissues to induce cytorrhysis to the vegetative tissues, wherein the solid-state water-soluble polymer is in a form of a crystal or powder, and said water-soluble polymer comprises polyethylene glycol having a molecular weight of 3,400 or greater.

2. The method of claim 1, wherein said water-soluble polymer further comprises a pH modifier.

3. The method of claim 2, wherein said pH modifier comprises at least one of acids, alkalis, or their salts.

4. The method of claim 1, wherein the mixing is performed at 45–65° C.

5. The method of claim 1, wherein said vegetative tissues are cut thinly or in a direction that facilitates movement of the polymer.

6. The method of claim 1, wherein said water-soluble polymer is mixed with the vegetative tissues, dehydrated, and separated with a centrifuge to separate dehydrated tissues and dehydrated exudates.

7. The method of claim 6, wherein the dehydrated tissues are ground to be in a paste state.

8. A method for dehydration of vegetative tissues, comprising mixing a solid-state water-soluble polymer with the vegetable tissues to induce cytorrhysis to the vegetative tissues, wherein the solid-state water-soluble polymer is in a form of a crystal or powder, and further comprising a low-molecular-weight dehydration aid, said low-molecular-weight dehydration aid comprising at least one of salt, sugar, or sugar alcohol and said water-soluble polymer comprises polyethylene glycol having a molecular weight of 3,400 or greater.

9. The method of claim 8, wherein said water-soluble polymer comprises at least one of polyethylene glycol, gum arabic, arabinogalactan, egg albumin, milk protein, or soybean protein.

10. The method of claim 8, wherein said water-soluble polymer comprises at least one of gum arabic, arabinogalactan, or egg albumin.

11. The method of claim 8, wherein said water-soluble polymer comprises at least one of milk protein or soybean protein.

12. A method for dehydration of vegetative tissues, comprising mixing a solid-state water-soluble polymer said water soluble polymer comprises polyethylene glycol having a molecular weight of 3,400 or greater with the vegetable tissues to induce cytorrhysis to the vegetative tissues, wherein the solid-state water-soluble polymer is in a form of a crystal or powder, said water-soluble polymer is mixed with the vegetative tissues, dehydrated, and separated with a centrifuge to separate dehydrated tissues and dehydrated exudates, and at least one of water, a concentrated dehydration solution of said polymer with a lowered viscosity, a concentrated sugar solution, and a salt solution is used for washing the separated dehydrated tissues.

* * * * *